United States Patent [19]

Allard et al.

[11] 4,428,672

[45] Jan. 31, 1984

[54] VARIABLE THRESHOLD WORKPIECE EXAMINATION

[75] Inventors: Martin E. Allard, Brixham; Joseph A. Wilcox, Havant, both of England

[73] Assignee: Brent Chemicals International Limited, Buckinghamshire, England

[21] Appl. No.: 311,739

[22] Filed: Oct. 15, 1981

[30] Foreign Application Priority Data

Oct. 17, 1980 [GB] United Kingdom ............... 8033661

[51] Int. Cl.$^3$ ............................................. G01N 21/88
[52] U.S. Cl. ................................. 356/237; 250/302; 250/358.1; 250/563
[58] Field of Search ............... 250/302, 358.1, 359.1, 250/360.1, 562, 572, 563; 356/317, 318, 237, 239, 430, 431, 429; 358/106

[56] References Cited

U.S. PATENT DOCUMENTS

3,774,030 11/1973 O'Connor et al. ............... 250/302
4,207,593 6/1980 Deutsch et al. ............... 250/562 X Primary Examiner—F. L. Evans
Assistant Examiner—L. A. Dietert
Attorney, Agent, or Firm—Sughrue, Mion, Zinn, Macpeak and Seas

[57] ABSTRACT

An automated system for examining a workpiece 6 treated so that flaws are revealed by concentrations of indicator on its surface scans the workpiece surface to provide an output signal representative of the luminance of surface regions. These are stored in a memory 12 and first and second signals representative of the average luminance of a number of regions A, B, C, and E, F, G on opposite sides of a central region D are formed. The first and second average signals are compared to determine which one represents the greatest concentration of indicator and the selected signal is used to derive a threshold value which is compared with the output signal representative of the luminance of the central region D. A flaw is indicated when the central region luminance signal is greater than the threshold value. Using this variable threshold technique based on the highest average of the surroundings it is possible to achieve great selectivity in the examination of the workpiece which takes into account differences in the background levels of indicator and enables automatic scanning of a workpiece which is as or more sensitive than the human eye.

18 Claims, 5 Drawing Figures

Fig.1

| A | B | C | D | E | F | G |

*Fig.2*

|   |   |   | H |   |   |   |
|   |   |   | I |   |   |   |
|   |   |   | J |   |   |   |
| A | B | C | D | E | F | G |
|   |   |   | K |   |   |   |
|   |   |   | L |   |   |   |
|   |   |   | M |   |   |   |

VARIABLE THRESHOLD WORKPIECE EXAMINATION

In non-destructive testing a workpiece is frequently treated so that flaws in it are revealed by concentrations of an indicator on its surface. This can be achieved by magnetic particle testing and dye penetrant testing. Magnetic particle testing can be applied to any magnetic material and in this technique a magnetic field is established through the workpiece to be tested. When the field crosses a crack or discontinuity such as a non-metallic inclusion, opposite magnetic poles form on opposite sides of the crack or non-metallic inclusion. This localised magnet attracts and holds an indicator including fine magnetic particles which are sprayed, washed or dusted onto the surface of the workpiece. Thus, concentrations of the indicator collect adjacent any cracks or discontinuities and these concentrations can be made easier to detect by the indicator also including a dye or pigment. The dye penetrant method is suitable for detecting flaws in workpieces made of non-porous materials and this is suitable for both magnetic and non-magnetic metals and alloys and may also be used with non-metallic materials. After cleaning, degreasing and drying, the workpiece is dipped into, sprayed, brushed or somehow coated with an indicator such as a penetrating liquid containing a dye. This indicator coats the surface and enters any surface cracks or flaws. The object is then treated in aqueous or solvent systems to remove excess indicator from the surface, dried and usually developed by applying a material to the surface of the workpiece which draws the indicator retained in the flaws to the surface.

When workpieces have been treated in either of these ways, the result is that any flaw in the workpiece is indicated by a local concentration of indicator on the surface of the workpiece. To enhance the visibility of such a local concentration of indicator its characteristics are chosen so that they contrast with the background of the workpiece or the developer. Thus, in dye penetrant techniques, the indicator typically includes a dark red dye and the developer, after drying, appears as a white powder. In this case any flaws appear as red spots or lines against a generally white background. The developer may also fluoresce when illuminated by ultraviolet light. In this case when the surface of the workpiece is illuminated by ultraviolet light the concentrations of indicator containing the red dye appear as intense dark spots or lines against a light background. A further way of enhancing the visibility of a local concentration of indicator against the background of the workpiece is for the indicator to include a luminescent dye or pigment which absorbs electromagnetic radiation of one wavelength and emits electromagnetic radiation of a longer wavelength. Typically the luminescent material is fluorescent and it preferably absorbs ultraviolet radiation and emits visible light.

Recently, automated application and processing techniques have been achieved for both magnetic particle and dye penetrant types of non-destructive testing and there have been repeated attempts to provide some automated flaw detection system but, so far, none of these have achieved commercial success. Therefore, at present, all commercial non-destructive testing systems include, at some stage, a visual inspection performed by a person who manipulates the workpiece whilst inspecting the workpiece to locate local concentrations of indicator. Inspection by eye has various disadvantages including the limitation of the speed of the inspection, and errors associated with tiredness, lack of concentration and a variability caused by variations in the visual acuity and subjective judgement of the observers.

Thus, it is desirable to provide some automated inspection system that does not rely on a human observer to enable the entire non-destructive testing process to be automated. Earlier proposals which have usually involved some form of scanning operation on the surface of the workpiece have failed or have been severely limited in their application because it has proved impossible to separate the presence of a local concentration of indicator from the background which is often contaminated by traces of the indicator remaining on the surface of the workpiece as a result of variations in the efficiency of the washing of the workpiece to remove the excess indicator. One such proposal is disclosed in U.S. Pat. No. 4,207,593. In the proposal described in this specification the surface of a workpiece is scanned and an electrical signal representative of the luminance of one region of a workpiece is compared with an average signal produced by averaging signals representative of the luminance of regions of the workpiece adjacent the one region. This system together with other previously proposed automatic systems are particularly susceptible to error when trying to distinguish the presence of a flaw located adjacent an edge of the workpiece or the edge of a part of the workpiece. In this case, the automatic sensor has to distinguish between a response outside the edges of the workpiece or part of the workpiece and the edge of an inefficiently washed workpiece or an inefficiently washed part of the workpiece which includes some indicator on its surface. The previous automatic inspection systems tend to record such an inefficiently washed workpiece as flawed and thus previous automatic inspection systems are easily deceived and unreliable in practice.

According to a first aspect of this invention a method of examining a workpiece that has been treated so that the flaws in it are revealed by concentrations of indicator on its surface to examine it for the presence of flaws, includes scanning the surface of the workpiece and providing an output signal representative of the luminance of regions of the surface of the workpiece, storing the output signals representative of the luminance of the regions of the workpiece in a memory, forming a first average signal representative of the average luminance of a number of regions to one side of one region, forming a second average signal representative of the average luminance of a number of regions to the other side of the said one region, comparing the first and second average signals to determine which of the first and second average signals indicates the greater concentration of indicator, selecting whichever of the first and second average signals indicates the greater concentration of the indicator and using this to derive a threshold value, comparing the derived threshold value with the output signal representative of the luminance of the said one region, and indicating that a flaw is present in the workpiece when the output signal representative of the luminance of the said one region indicates a greater concentration of indicator than does the threshold value.

By using this technique of analysing the signals representative of the luminance of regions of the workpiece it is possible to achieve great selectivity in the monitoring of the workpiece to provide a method of automatically scanning the workpiece which is as sensitive as, or better than, the human eye and which is more reliable and consistent in its performance. By forming a first average signal representative of the average luminance of a number of regions to one side of the said one region and then forming a second average signal representative of the average luminance of a number of individual regions to the other side of the said one region, and comparing the first and second average signals and using whichever indicates the greater presence of indicator to derive a threshold value, a flaw positioned adjacent the edge of the workpiece does not create any particular problem. Taking the case of the said one region being located on the edge of the workpiece and the said one region being the location of a fault, the regions to the one side of the said one region are typically a constant background behind the workpiece which is chosen to have the same or a similar luminance to that of an adequately washed workpiece. The average response from the regions to the other side of the said one region is the background luminance of the workpiece and if the workpiece has been inadequately washed this background luminance signal indicates a considerable presence of indicator on the surface of the workpiece. In this circumstances, it is the background signal corresponding to the badly washed workpiece which is used to derive the threshold value and when this threshold value is compared with the luminance of the said one region which includes the presence of the fault, the luminance of the said one region indicates a very much stronger presence of indicator on the surface than does the derived threshold value and hence the flaw is detected.

The number of regions of the workpiece to the one and the other side of the said one region that are used to form the average signals is usually determined by a compromise between accuracy and the time to perform the analysis of the results. Typically, the number ranges from three to five and it has been found that when three regions are averaged, an adequate accuracy is achieved. Preferably the regions are scanned repeatedly and the results from a number of such scans are buffered and averaged before they are used. This improves the accuracy and reliability of the determination of a flaw. The output signals representative of the luminance of the regions immediately adjacent the said one region and on both sides of the one region may not be used in the determination of the first and second average signals.

A greater sensitivity, accuracy and reliability can be achieved if the output signals representative of the luminance of the regions of the workpiece are analysed from more than one direction and, in this case, it is preferred that the signals are analysed with respect to two axes which are mutually perpendicular. Thus, as an example of this, in addition to forming a first average signal representative of the average luminance of a number of regions to the one side of the said one region and forming a second average signal representative of the average luminance of a number of regions to the other side of the said one region and comparing the first and second average signals to determine which of the first and second average signals indicates the greater concentration of indicator, selecting whichever of the first and second average signals indicates the greater concentration of the indicator and using this to derive the threshold value, it is also possible to form a third average signal representative of the average luminance of a number of regions above the said one region, form a fourth average signal representative of the average luminance of a number of individual regions below the said one region and compare the third and fourth average signals to determine which of the third and fourth average signals indicates the greater concentration of indicator, selecting whichever of the third and fourth average signals indicates the greater concentration of the indicator and using this to derive another threshold value. In this case, this other derived threshold value is also compared with the output signal representative of the luminance of the said one region, and a flaw is indicated when the luminance of the said one region indicates a greater concentration of indicator than does either of the derived threshold values.

In addition to carrying out determinations along two mutually perpendicular axes, it is also possible to carry out determinations along more than two axes, for example, along four axes separated by 45° from one another. In general, the greater the number of axes along which the determination is carried out the greater the sensitivity, accuracy and reliability of the determination. However, the greater the number of determinations the greater the time that is taken for each test and therefore, a compromise has to be reached. We have found that it is usually sufficient to carry out a determination along a single axis even though it is theoretically possible not to observe a perfectly straight crack or flaw extending precisely along the axis of the determination.

Preferably the output signal representative of the luminance of the said one region is also compared with a fixed threshold value representing a high concentration of indicator on the surface of the workpiece. If the output signal representative of the luminance of the said one region indicates the presence of a greater concentration of the indicator than that represented by this fixed threshold value an indication of a flaw is given which overrides the result of the comparison of the output signal representative of the luminance of the said one region with the average signals. This fixed threshold value thus provides a flaw indication in the case where the workpiece is so inadequately washed or prepared that the indicator is present at a high level of concentration over its entire surface. It also indicates the presence of a flaw extending over a very large area of the workpiece that could otherwise possibly be interpreted as a large badly washed part of the surface of the workpiece.

According to a second aspect of this invention, an apparatus for examining a workpiece that has been treated so that flaws in it are revealed by concentrations of indicator on its surface to identify the presence of flaws includes means for scanning the surface of the workpiece and providing output signals representative of the luminance of regions of the surface of the workpiece; a memory for storing the output signals representative of the luminance of the regions of the workpiece; means to form a first average signal representative of the average luminance of a number of regions to one side of one region, to form a second average signal representative of the average luminance of a number of regions to the other side of the said one region, to compare the first and second average signals to determine which of the first and second average signals indicates the greater concentration of indicator, to select whichever of the first and second average signals indicates the greater concentration of the indicator and use this value to derive a threshold value, to compare the derived threshold value with the output signals representative of the luminance of the said one region, and to output a signal dependent upon the result of this comparison; and, response means responsive to the signal output by the means.

The means to form a first average signal representative of the average luminance of a number of regions to one side of one region, to form a second average signal representative of the average luminance of a number of individual regions to the other side of the said one region, to compare the first and second average signals to determine which of the first and second average signals indicates the greater concentration of indicator, to select whichever of the first and second signals indicates the greater concentration of the indicator and use this value to derive a threshold value, to compare the derived threshold value with the output signal representative of the luminance of the one region, and to output a signal dependent upon the result of this comparison is formed by a programmed computer.

In accordance with a third aspect of this invention an apparatus for examining a workpiece that has been treated so that flaws in it are revealed by concentrations of indicator on its surface to identify the presence of flaws includes means for scanning the surface of the workpiece and providing output signals representative of the luminance of regions of the surface of the workpiece, a memory for storing the output signals representative of the luminance of the regions of the workpiece, first averaging means forming a first average signal representative of the average luminance of a number of regions to one side of one region, second averaging means for forming a second average signal representative of the average luminance of a number of regions to the other side of the said one region, means for comparing the first and second average signals to determine which of the first and second average signals indicates a greater concentration of indicator, means to select whichever of the first and second average signals indicates the greater presence of indicator and derive a threshold value, a comparator for comparing the derived threshold value and the output signal representative of the luminance of the one region and outputting a signal dependent upon the result of this comparison, and response means responsive to the output of the comparator.

Preferably the apparatus also includes means for generating a fixed threshold value, and means for comparing the output signal representative of the luminance of the said one region of the surface of the workpiece with this fixed threshold value and outputting a signal dependent upon the result of this comparison. The means for comparing may once again be formed as part of the programmed computer or, alternatively it may be formed by a comparator. The output signal dependent upon the result of the comparison with the fixed threshold value is preferably gated with that dependent upon the result of the comparison with the derived threshold value so that if either or both comparisons indicate the presence of a greater concentration of the indicator on the surface of the workpiece a flaw indication is given to the response means. The response means may be arranged to reject a workpiece which includes the presence of a flaw or, it may be arranged to provide an indication or an alarm that the workpiece includes a flaw, or both of these.

The means for scanning the surface of the workpiece and providing output signals representative of the luminance of the regions of the surface of the workpiece may be formed by means to flood the surface of the workpiece with visible or near visible electromagnetic radiation and means for scanning the surface of the workpiece to monitor the luminance of regions of the workpiece. In this case, the means for scanning the surface of the workpiece may include an electronic camera such as a television-type camera including a photoconductive pickup tube, which may also include an image intensifier such as a VC 2000 low light camera manufactured by Visual Contact Ltd of Great Britain, or a line scan camera including a self-scanning array of charged coupling devices such as that made by Fairchild Corporation of the United States of America and sold as their type CCD1100 Camera.

However, it is preferred that a source of intense visible or near visible electromagnetic radiation is scanned in a raster pattern over the surface of the workpiece and that one or more sensors are provided surrounding the workpiece to monitor the light emitted from the surface of the workpiece. In this case, the means scanning the intense radiation over the surface of the workpiece includes means to encode its position and couple this encoded position with the output from the sensors, to enable the sensors to be able to identify their response with particular regions on the surface of the workpiece that are, at that instant, being irradiated by the source of intense radiation. Preferably, the source of intense radiation is formed by a laser.

Preferably the apparatus also includes orienting means to present all faces of the workpiece in sequence and typically the orienting means is arranged to rotate the workpiece successively through 90° so that the workpiece is turned through 360°, and then turn the workpiece so that its two end faces are presented in succession. Such a system ensures that the workpiece is subjected to the minimum possible number of scans consistent with the scan impinging upon each and every part of the workpiece. However, depending upon the exact shape of the workpiece its orientation during scanning can be matched to its particular shape so that the most effective scanning of the workpiece is carried out. As an example of this, if the workpiece has the form of a hexagonal prism it may be more convenient to present each of its six longitudinal faces to the scanning means in turn and then its two ends.

The use of one or more sensors, typically four or six, together with the orienting means to present all surfaces of the workpiece, firstly ensures that the radiation from the source impinges upon each and every part of the surface of the workpiece, and secondly ensures that the radiation emitted from the workpiece is detected by the sensors.

Preferably the apparatus forms part of a completely automated system for non-destructive testing of workpieces including means for selectively applying indicator to the surface of the workpiece so that flaws in the workpiece are revealed by concentrations of the indicator and means to raise an alarm or reject the workpiece if a flaw is detected.

Examples of a method and apparatus in accordance with the invention will now be described with reference to the accompanying drawings, in which.

This example of an automated non-destructive testing apparatus includes an automated application and processing apparatus for applying an indicator containing fine magnetic particles together with a dye or a penetrant together with a dye onto the surface of the workpiece and for removing excess indicator from the surface of the workpiece. These portions of the apparatus are conventional and will not be described in detail. The apparatus also includes a scanning apparatus for examining the workpiece for the presence of any local concentration of indicator on its surface which indicate the presence of flaws.

Figure 1:
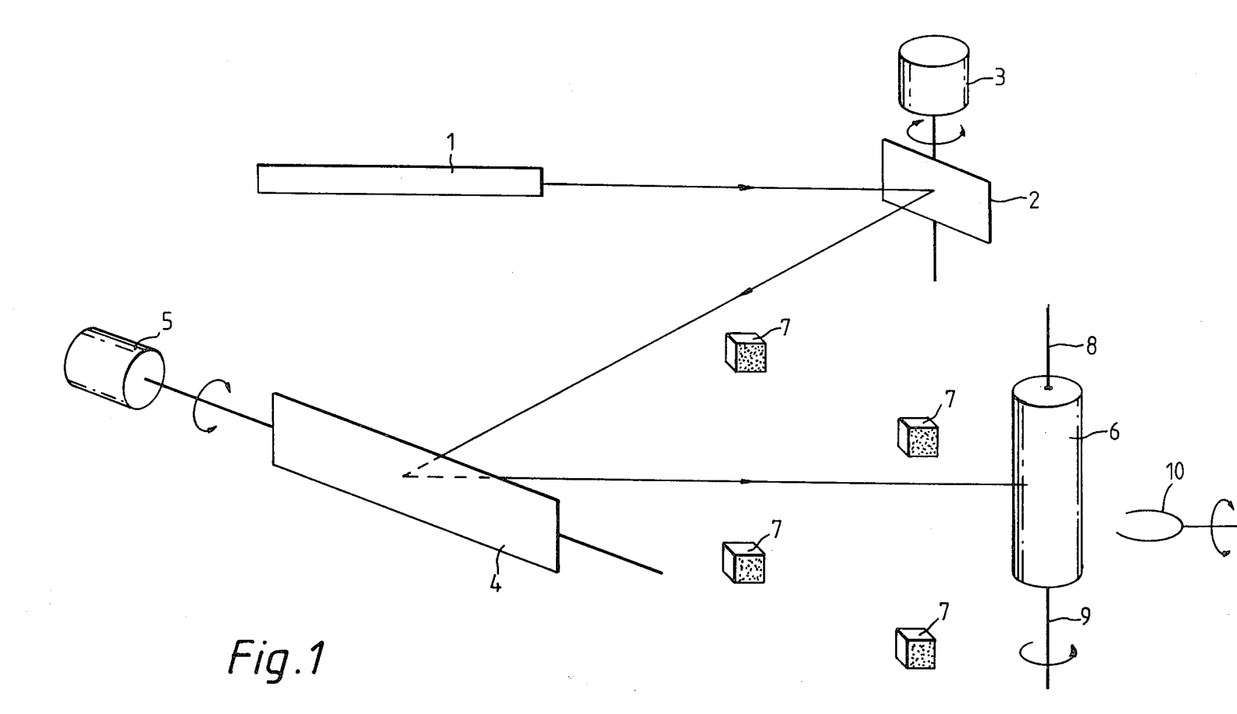
FIG. 1 is a diagrammatic perspective view of one example of scanning apparatus.

A first example of scanning apparatus is used with an indicator containing a fluorescent material which absorbs ultraviolet light and emits visible radiation.

The scanning apparatus comprises a helium-cadmium laser 1 tuned to emit ultraviolet radiation, a first oscillating scanning mirror 2 which is driven by a drive 3 to oscillate rapidly about a vertical axis and a second oscillating scanning mirror 4 which is driven by a drive 5 to oscillate at a slower rate about a substantially horizontal axis. Typically the scanning mirror 2 oscillates 256 times faster than the oscillation of the scanning mirror 4 which results in the light from the helium-cadmium laser 1 being scanned across a workpiece 6 in a raster pattern having 256 lines. The beam of light from the helium-cadmium laser 1 is preferably collimated to provide a beam approximately 1.4 mm in diameter. Thus, with the adjacent lines of the raster pattern just touching one another, this arrangement is able to scan workpieces 6 having a major dimension of 25 to 30 cm.

The scanning mirrors 2 and 4 may include angular position encoders to encode the instantaneous angular position of the mirrors 2 and 4, but preferably a driving signal applied to the drives 3 and 5 is used to provide an indication of the instantaneous position of the beam of light from the laser 1. The scanning apparatus also includes four photomultiplier tubes 7 facing the surface of the workpiece upon which the laser beam impinges. The scanning apparatus is mounted in a light tight matt black painted chamber. The outputs from the photomultiplier tubes 7 are added together and their combined output signal is a measure of the visible light emitted by fluorescence of any indicator present on the part of the surface of the workpiece 6 that is, at any particular instant, being irradiated by ultraviolet light from the laser 1.

Naturally if the indicator contains, for example, a red dye then the laser 1 is preferably tuned to emit blue light at a wavelength of around 442 nm and the scanning apparatus is then housed in a light tight white painted or light reflecting chamber.

Another example of scanning apparatus is the use of an electronic camera. In this case the workpiece is flooded with ultraviolet light when the indicator contains a fluorescent dye or flooded with visible light when the indicator contains a coloured dye. Preferably the visible light contrasts in colour with the colour of the dye so that, for example, a blue or green light is used when the indicator contains a red dye. The camera is directed towards the workpiece and forms an image of the workpiece on its photoconductive pickup. The photoconductive pickup is scanned electronically to provide an analogue signal corresponding to variations in luminance of the surface of the workpiece. A typical electronic camera that is suitable when the indicator includes a fluorescent dye is a type VC 2000 low light camera manufactured by Visual Contact Ltd of Great Britain. Again the workpiece and camera is mounted in a light tight chamber which, when the indicator fluoresces and emits visible light is painted matt black, and when it absorbs light is painted white or is light reflecting.

No matter which type of scanner is used the output is similar in that it comprises an analogue signal corresponding to the luminance of regions of the area scanned.

The scanning apparatus also includes a handling mechanism to hold the workpiece 6 in position and to orient the workpiece 6 with respect to the scanning laser beam or to the camera so that all of the workpiece is presented to the scanning laser beam or camera. A particular example of handling apparatus may include a pair of supports 8 and 9 to engage the ends of the workpiece 6 with the supports 8 and 9 connected to a drive to rotate the workpiece 6 about its longitudinal axis. The handling mechanism also includes a pair of jaws 10 which can grip the middle of the workpiece 6 and turn the workpiece 6 so that its ends are presented towards the scanning laser beam or camera. The supports 8 and 9 and the jaws 10 may also include position encoders. The handling apparatus may be set up to perform a repetitive sequence of operations which is arranged to present the entire surface of the workpiece to the scanning laser beam or camera. Alternatively, the drive for the supports 8 and 9 and the jaws 10 may be inter-active and controlled by a computer. In this way the information gained by the scanning can be correlated with the position of the workpiece with that of the scanning beam or camera.

Figure 3:
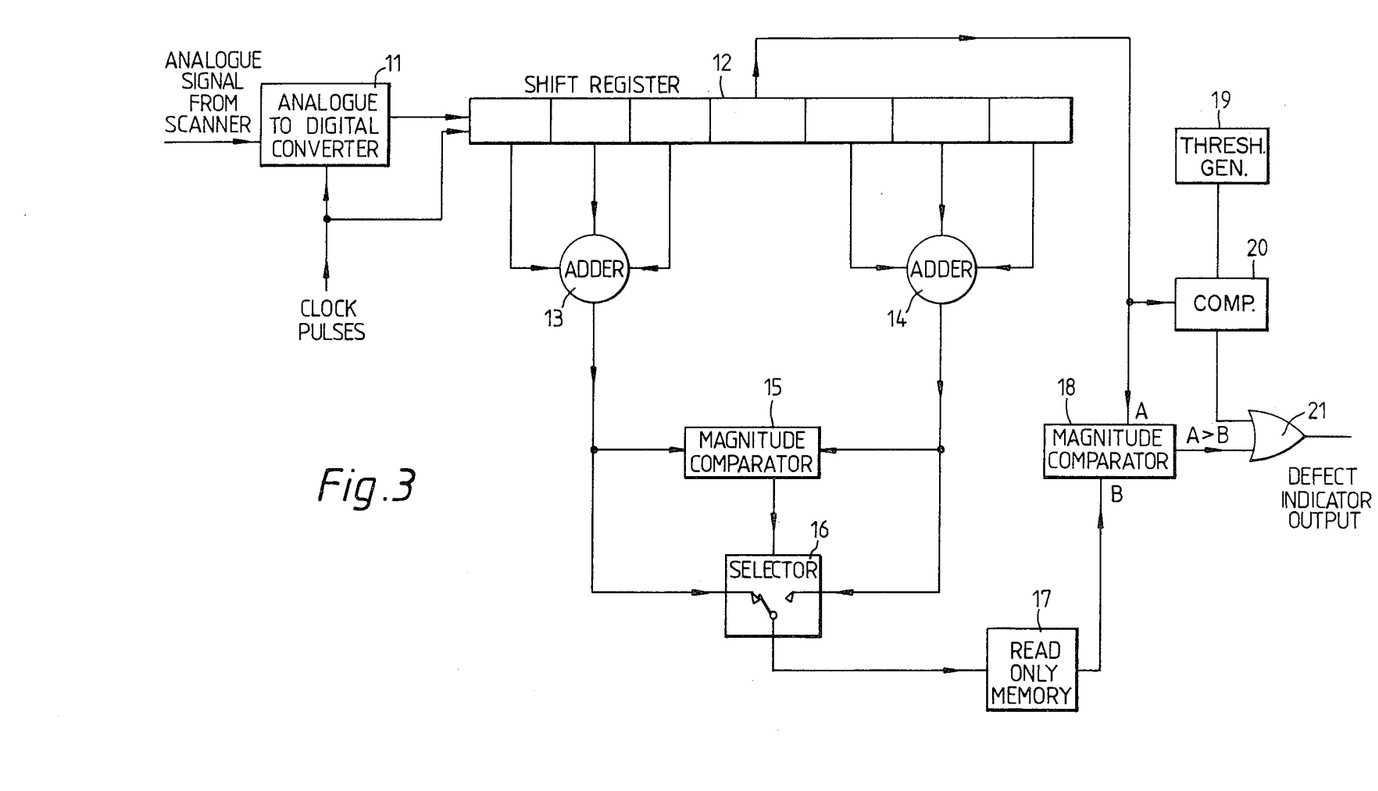
FIG. 3 is a block diagram of one example of a data handling logic circuit.

A method and one example of an apparatus for analysing the scanning information obtained will now be described. The analogue signal obtained from the scanner is applied to an analogue to digital converter 11. If the indicator, illuminant, and scanning system is such as to produce a negative image, it is preferably electrically inverted at this stage; so that a concentration of indicator always appears as a positive signal even when this is because the indicator absorbs light. The analogue to digital converter 11 may be clocked by a clock signal derived from the scanning apparatus or, alternatively, may be clocked from an external clock. The output from the analogue to digital converter 11 is connected to a seven stage shift register 12 which also receives the clock signal to shift the information along the shift register 11. An adder 13 is connected to the first second and third stages of the shift register 12 and a second adder 14 is connected to the fifth sixth and seventh stages of the shift register 12. The outputs from the adders 13 and 14 are compared in a magnitude comparator 15 and this magnitude comparator 15 controls a selector 16 which selects the output from the adder 13 or the adder 14, whichever is the greater. The output from the selector 16 is applied to a look-up table or read-only memory 17 and the output from the read-only memory 17 is compared with the output from the fourth stage of the shift register 12 in a magnitude comparator 18.

Figure 2:
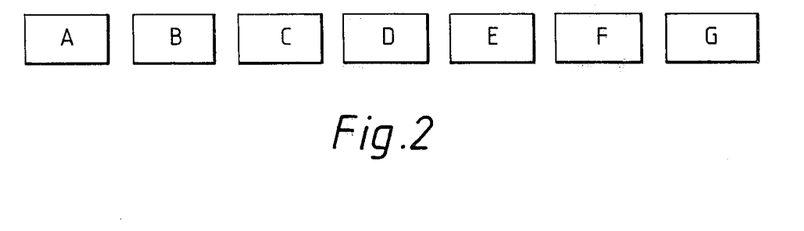
FIG. 2 is a diagram showing a typical scanning pattern.

Thus the signals from the scanning apparatus after conversion into digital form in the analogue to digital converter 11 is applied to the shift register 12. As the laser beam moves over the surface of the workpiece or as the image in the camera is scanned the resulting data is shifted along the shift register 12 with each stage of the shift register corresponding to one element in the scan of the scanning apparatus. FIG. 2 shows seven elements of a scan labelled A to G and the data corresponding to these elements is contained in the shift register 12. The adder 13 adds together the data corresponding to the elements A, B and C whilst the adder 14 adds the data corresponding to the elements E, F and G. Whichever sum is the greater is then applied to the look-up table 17 which, in response to the magnitude of the sum output from the adder 13 or 14 outputs a threshold signal. The output from the fourth stage of the shift register 12 which represents the output of the scanning apparatus for the element D of the scan is then compared to this derived threshold value from the look-up table 17 in the magnitude comparator 18 and, if the magnitude of the data from the position D is greater than the derived threshold value an output is obtained from the magnitude comparator 18.

A fixed threshold generator 19 generates a reference threshold value corresponding to the output signal from the scanning apparatus when a high level of indicator is present. The data from the element D is compared with this reference threshold value in a magnitude comparator 20 which provides an output when the data exceeds the reference threshold value. The output from the magnitude comparator 20 is fed to one input of an OR gate 21 and the output of the comparator 18 is fed to the other input of the OR gate 21. The output from the OR gate 21 is then applied to an alarm circuit (not shown) to give an indication that a flaw is present in the workpiece 6. As soon as a flaw is detected the workpiece may be rejected but it is preferred that the scan is continued over the entire workpiece 6.

At the completion of a scan over the surface of the workpiece, the workpiece is then rotated, for example about its longitudinal axis through 90° by the supports 8 and 9, and a further scan carried out. This process is repeated with the workpiece 6 being rotated through 90° until it has been rotated through 360°. At this point the jaws 10 are used to turn the workpiece 6 so that one of its ends is presented towards the laser beam or camera and the scanning process repeated on an end face of the workpiece 6. Finally the jaws are rotated through 180° to preset the other end face of the workpiece 6 to the laser beam or camera. The output from the OR gate 21 may be arranged to reject or accept the workpiece 6 automatically at the completion of its scanning.

In practice, it is always arranged that the area of the scan is rather greater than the face of the workpiece 6 that is presented to the scanning laser beam or camera at any instant so that there are always at least three scanning elements between the start of each line of the scan and the edge of the workpiece 6. However, the apparatus may include means to inhibit a defect indication being given when the scan is within four elements from the end of each line of the scan.

An alternative example of apparatus for analysing the scanning information uses a programmed microprocessor. The microprocessor is programmed so that the output signals from the scanning apparatus are subjected to the same sequence of averaging and comparison steps as described above with reference to the logic circuits. An example of a microprocessor capable of performing this sequence of steps is a Zilog Z80A manufactured by Zilog of the United States of America.

Figure 4:
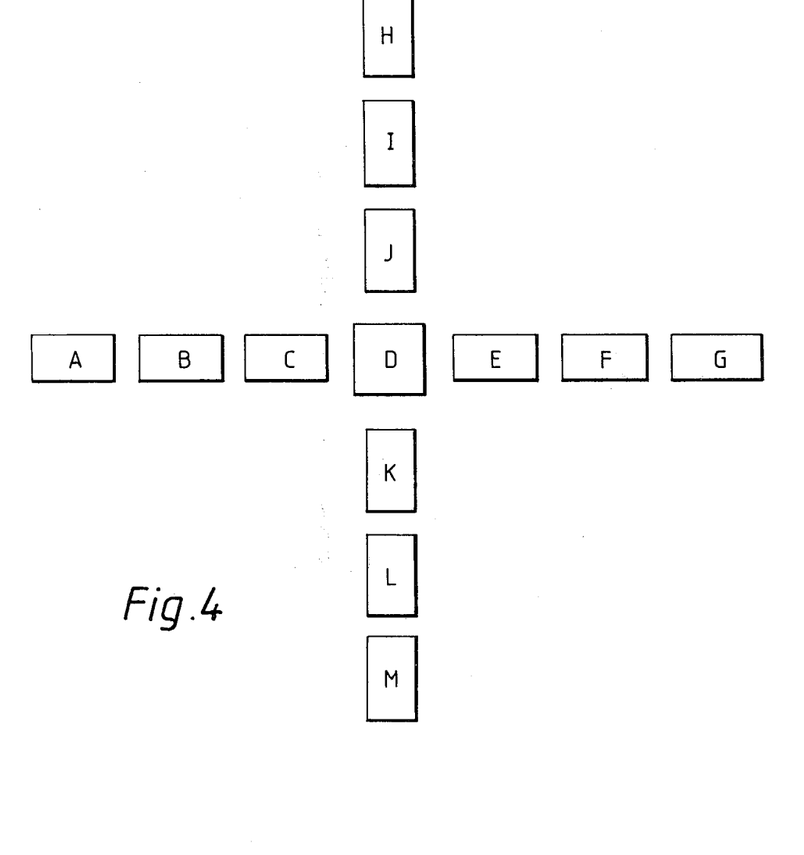
FIG. 4 is a diagram showing a modification of the scanning pattern in the modification.

In a modification of the data handling arrangements of the device in accordance with this invention, instead of being applied directly to logic circuitry or to a microprocessor, the output of the analogue to digital converter 11 is loaded into a digital frame store (not shown) and then the data in this digital frame store is addressed and operated on by, in effect, analysing arrangements which are substantially those already described, the outputs of which are gated together through an OR gate so that a defect indication is given when a positive output is obtained from either of the analysing arrangements. In this case, the digital frame store is addressed to obtain information from the elements to one and the other side of the said one element and from elements above and below the said one element as shown in FIG. 4. Thus, in effect, the workpiece 6 is scanned in two mutually perpendicular directions as shown by the diagram in FIG. 4.

Figure 5:
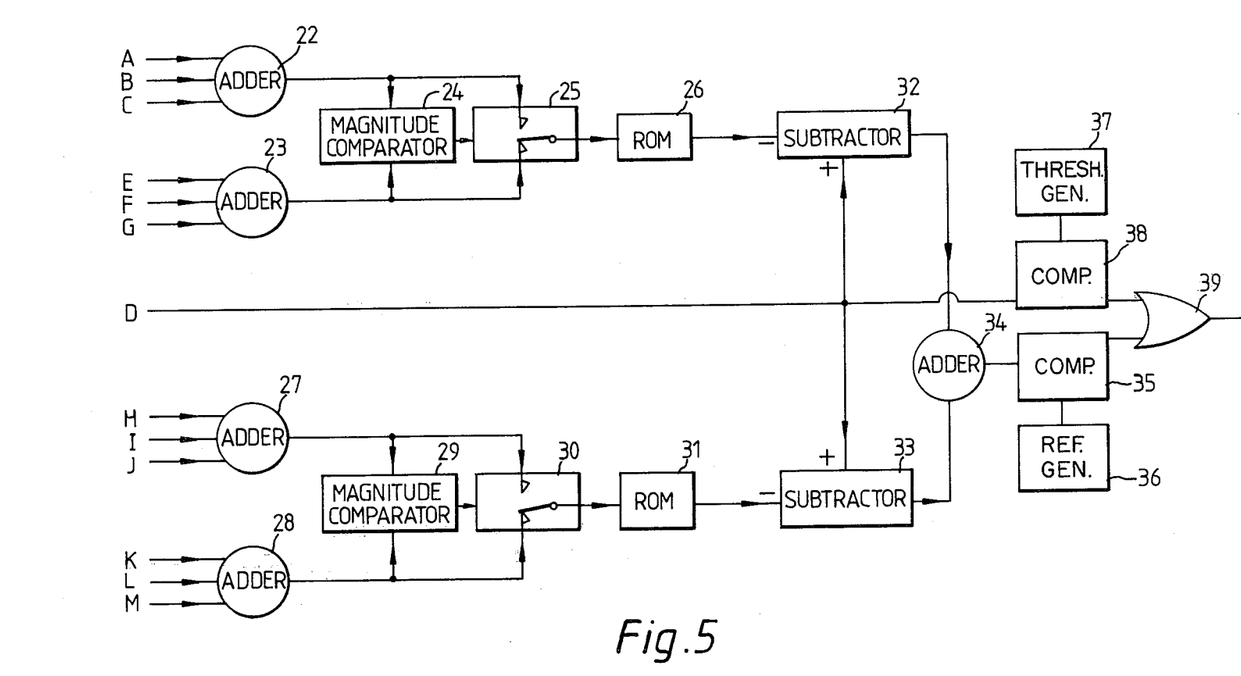
FIG. 5 is a block diagram of another example of data handling logic circuit.

As an example of this modification of the data handling arrangements the logic elements that are required to perform it are shown in FIG. 5. In this example, the output from the analogue to digital converter 11 is loaded into a digital frame store (not shown). Outputs from addresses in the digital frame store corresponding to the position of the elements A to M as shown in FIG. 4 are then used in the circuit of FIG. 5. Data corresponding to the elements A, B and C are added in an adder 22 whilst data corresponding to elements E, F, G are added in an adder 23. The magnitude of the output of the adder 22 and the adder 23 are compared in a magnitude comparator 24 which controls a selector 25 so that the output of whichever of the adders 22 and 23 is the greater is applied to a look-up table or read only memory 26. Thus, the adders 22 and 23, the magnitude comparator 24, the selector 25, and the look-up table 26 are analogous to the adders 13 and 14, the magnitude comparator 15, the selector 16 and the look-up table 17 of the example shown in FIG. 3.

Similarly, an adder 27 adds the data from the regions H, I and J and an adder 28 adds the data from the regions K, L and M. These are applied to a magnitude comparator 29 and a selector circuit 30 followed by a look-up table or read-only memory 31. Thus, the output from the look-up table 26 provides a derived threshold for the scan in the horizontal direction whilst the output from the look-up table 31 provides a derived threshold from a scan in the vertical direction. These are applied, respectively, to a subtractor 32 and a subtractor 33. The output from the element D in the centre of both scans is also applied to the subtractors 32 and 33. The output from the subtractors 32 and 33 is added together in an adder 34 and compared in a comparator 35 against a fixed reference. The outputs from the subtractors 32 and 33 can be considered as signal representing the "probability" of a defect and thus, by adding these two signals together in an adder 34 an indication can be obtained of the probability that a defect is present in the scanning element D. This signal representing a probability can then be compared with a predetermined reference produced by a reference generator 36 in the comparator 35 to give a defect output.

A fixed threshold generator 37 which corresponds to the fixed reference generator 19 outputs a reference signal corresponding to the output signal from the scanning apparatus when a high level of indicator is present. The data from the element D is compared with this reference threshold value in a comparator 38 which outputs a signal when the data exceeds the reference threshold value. The output from the comparator 38 and the output from the comparator 35 are fed to inputs of an OR gate 39. The output from the OR gate 39 is then applied to an alarm circuit (not shown) to give an indication that a flaw is present in the workpiece 6.

We claim:

1. A method of examining a workpiece that has been treated so that the flaws in it are revealed by concentrations of indicator on its surface to examine it for the presence of flaws, including:

scanning the surface of said workpiece and providing an output signal representative of the luminance of regions of said surface of said workpiece;

storing said output signals representative of said luminance of regions of said workpiece in a memory;

forming a first average signal representative of average luminance of a number of said regions to one side of one region;

forming a second average signal representative of average luminance of a number of regions to the other side of said one region;

comparing said first and second average signals to determine which of said first and second average signals indicates the greater concentration of said indicator;

selecting whichever of said first and second average signals indicates said greater concentration of said indicator and using this to derive a threshold value;

comparing said derived threshold value with said output signal representative of said luminance of the said one region; and, indicating that a flaw is present in said workpiece when said output signal representative of said luminance of said one region indicates a greater concentration of indicator than does said derived threshold value.

2. The method of claim 1, wherein said number of regions of said workpiece to said one and said other side that are used to form said average signals is in a range from three to five.

3. The method of claim 1, wherein said regions are scanned repeatedly and the results from a number of such scans are buffered and averaged before they are used.

4. The method of claim 1, wherein said output signals representative of said luminance of said regions of said workpiece are analysed with respect to two axes which are mutually perpendicular.

5. The method of claim 4, which also includes:

forming a third average signal representative of average luminance of a number of regions above said one region;

forming a fourth average signal representative of average luminance of a number of individual regions below said one region;

comparing said third and fourth average signals to determine which of said third and fourth average signals indicates the greater concentration of said indicator;

selecting whichever of said third and fourth average signals indicates the greater concentration of said indicator and using this to derive another threshold value;

comparing said other derived threshold value with said output signal representative of said luminance of said one region; and, indicating that a flaw is present in said workpiece when said output signal representative of said luminance of said one region indicates a greater concentration of indicator than does either of said derived threshold values.

6. The method of claim 1 or 5, wherein said output signal representative of said luminance of said one region is also compared with a fixed threshold value representing a high concentration of indicator on said surface of said workpiece, an indication of a flaw being given if said output signal representative of the luminance of said one region indicates the presence of a greater concentration of said indicator than that represented by said fixed threshold value, this indication of a flaw overriding the result of said comparison of said output signal representative of said luminance of said one region with said derived threshold value.

7. An apparatus for examining a workpiece that has been treated whereby flaws in said workpiece are revealed by concentrations of indicator on its surface to thereby identify the presence of flaws including:

means for scanning said surface of said workpiece and providing output signals representative of the luminance of regions of said surface of said workpiece;

a memory for storing said output signals representative of the luminance of said regions of said workpiece;

means to form a first average signal representative of average luminance of a number of regions to one side of one region, to form a second average signal representative of average luminance of a number of regions to the other side of said one region, to compare said first and second average signals to determine which of said first and second average signals indicates a greater concentration of said indicator, to select whichever of said first and second average signals indicates said greater concentration of said indicator and use this said value to derive a threshold value, to compare said derived threshold value with said output signal representative of said luminance of said one region, and to output a signal dependent upon the result of this said comparison; and, response means responsive to said signal output by said means.

8. The apparatus of claim 7, wherein said means to form a first average signal representative of average luminance of a number of regions to one side of one region, to form a second average signal representative of average luminance of a number of individual regions to the other side of said one region, to compare said first and second average signals to determine which of said first and second average signals indicates a greater concentration of said indicator, to select whichever of said first and second signals indicates said greater concentration of said indicator and use this said value to derive a threshold value, to compare said derived threshold value with said output signal representative of said luminance of said one region, and to output a signal dependent upon the result of this said comparison is formed by a programmed computer.

9. An apparatus for examining a workpiece that has been treated whereby flaws in said workpiece are revealed by concentrations of indicator on its surface to thereby identify the presence of flaws including:

means for scanning said surface of said workpiece and providing output signals representative of the luminance of regions of said surface of said workpiece;

a memory for storing said output signals representative of said luminance of said regions of said workpiece;

first averaging means forming a first average signal representative of average luminance of a number of regions to one side of one region;

second averaging means for forming a second average signal representative of average luminance of a number of regions to the other side of said one region;

means for comparing said first and second average signals to determine which of said first and second average signals indicates a greater concentration of indicator; means to select whichever of said first and second average signals indicates a greater presence of indicator and derive a threshold value;

a comparator for comparing said derived threshold value and said output signal representative of said luminance of said one region and outputting a signal dependent upon the result of this comparison; and, response means responsive to said output of said comparator.

10. The apparatus of claim 7 or 9, which also includes:

means for generating a fixed threshold value;

means for comparing said output signal representative of said luminance of said one region of said workpiece with said fixed threshold value and outputting a signal dependent upon the result of this comparison; and, gating means for gating said output signal dependent upon said result of said comparison with said fixed threshold value and that dependent upon said result of said comparison with said derived threshold value whereby if at least one of said comparisons indicate the presence of a greater concentration of said indicator on said surface of said workpiece a flaw indication is given to said response means.

11. The apparatus of claims 7, 9 or 10 wherein said response means is arranged to reject a workpiece which includes the presence of flaws.

12. The apparatus of claim 7, 9 or 10 wherein said response means is arranged to provide an indication that the workpiece includes a flaw.

13. The apparatus of claim 7 or 9, wherein said means for scanning said surface of said workpiece and providing output signals representative of the luminance of said regions of said surface of said workpiece is formed by means to flood said surface of said workpiece with electromagnetic radiation selected from a group consisting of visible and near visible electromagnetic radiation and means for scanning said surface of said workpiece to monitor said luminance of regions of said workpiece.

14. The apparatus of claim 13, wherein said means for scanning said surface of said workpiece includes an electronic camera.

15. The apparatus of claim 7 or 9, wherein said means for scanning said surface of said workpiece and providing output signals representative of the luminance of said regions of said surface of said workpiece includes a source of intense electromagnetic radiation selected from a group consisting of visible and near visible electromagnetic radiation, means to scan light from said source in a raster pattern over said surface of said workpiece, and a number of sensors surrounding said workpiece to monitor light emitted from said surface of said workpiece.

16. The apparatus of claim 15, wherein said means scanning said light from said source in a raster pattern over said surface of said workpiece includes means to encode its position and couple this encoded position with said output from said sensors, to enable said sensors to be able to identify their response with particular regions on said surface of said workpiece that are, at that instant, being irradiated by light from said source.

17. The apparatus of claim 7 or 9, which also includes:

orienting means to present all faces of said workpiece in sequence.

18. The apparatus of claim 17, wherein said orienting means is arranged to rotate said workpiece successively through 90° whereby said workpiece is turned through 360° and subsequently turn said workpiece whereby its two ends are presented in succession.

* * * * *